(12) United States Patent
Seitz et al.

(10) Patent No.: US 10,736,504 B2
(45) Date of Patent: Aug. 11, 2020

(54) METHOD FOR DETERMINING THE PUPIL DIAMETER OF AN EYE WITH HIGH ACCURACY, AND CORRESPONDING APPARATUS

(71) Applicant: Rodenstock GMBH, Munich (DE)

(72) Inventors: Peter Seitz, Munich (DE); Markus Tiemann, Munich (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 16/620,744

(22) PCT Filed: Jun. 12, 2018

(86) PCT No.: PCT/EP2018/065425
§ 371 (c)(1),
(2) Date: Dec. 9, 2019

(87) PCT Pub. No.: WO2018/229021
PCT Pub. Date: Dec. 20, 2018

(65) Prior Publication Data
US 2020/0100671 A1 Apr. 2, 2020

(30) Foreign Application Priority Data
Jun. 12, 2017 (LU) ........................ 100287

(51) Int. Cl.
*A61B 3/00* (2006.01)
*A61B 3/11* (2006.01)
*A61B 3/14* (2006.01)

(52) U.S. Cl.
CPC ............ *A61B 3/112* (2013.01); *A61B 3/0025* (2013.01); *A61B 3/0041* (2013.01); *A61B 3/0058* (2013.01); *A61B 3/145* (2013.01)

(58) Field of Classification Search
CPC ......... A61B 3/11; A61B 3/112; A61B 3/0025; A61B 3/0058; A61B 3/10; A61B 3/14; A61B 3/145; A61B 3/0041
See application file for complete search history.

(56) References Cited

U.S. PATENT DOCUMENTS 5,469,234 A * 11/1995 Konishi ................... A61B 3/11
351/211
5,790,235 A  8/1998 Kirschbaum
(Continued)

FOREIGN PATENT DOCUMENTS

DE  69317570  10/1998
WO  2013087212  6/2013

OTHER PUBLICATIONS

Methot, S. et al., "The Pupillary Light Response Reveals the Focus of Covert Visual Attention", PLoS One, vol. 8, No. 10, Oct. 2013.
(Continued)

*Primary Examiner* — Jordan M Schwartz
(74) *Attorney, Agent, or Firm* — Diederiks & Whitelaw, PLC.

(57) ABSTRACT

The invention relates to a method for highly accurate determining of a pupil diameter of an eye, using a camera system for spatial capturing of objects, the method including: imaging stereoscopic capturing of an eye region, wherein for an eye of the eye region a first and a second stereoscopic image arise. For each of the two stereoscopic images the method further includes: Transferring of the captured eye region into a color space. Determining of a region, within the captured eye region, as a region within a pupil of the captured eye region. Determining of a closed outer edge of the region within the pupil. Iterative determining of a closed outer pupil edge. The invention further relates to a corresponding device.

18 Claims, 11 Drawing Sheets

(56) References Cited

U.S. PATENT DOCUMENTS

| | | |
|---|---|---|
| 7,909,460 B1 | 3/2011 | Wada |
| 2009/0006508 A1* | 1/2009 | Youssefi .............. A61B 3/0025 708/132 |
| 2019/0347824 A1* | 11/2019 | Xue ........................ G06K 9/38 |

OTHER PUBLICATIONS

Nguyen, A. H. et al., "Model Control of Image Processing: Pupillometry", Computerized Medical Imaging and Graphics, vol. 17, No. 1, pp. 21-33, Jan. 1993.

\* cited by examiner

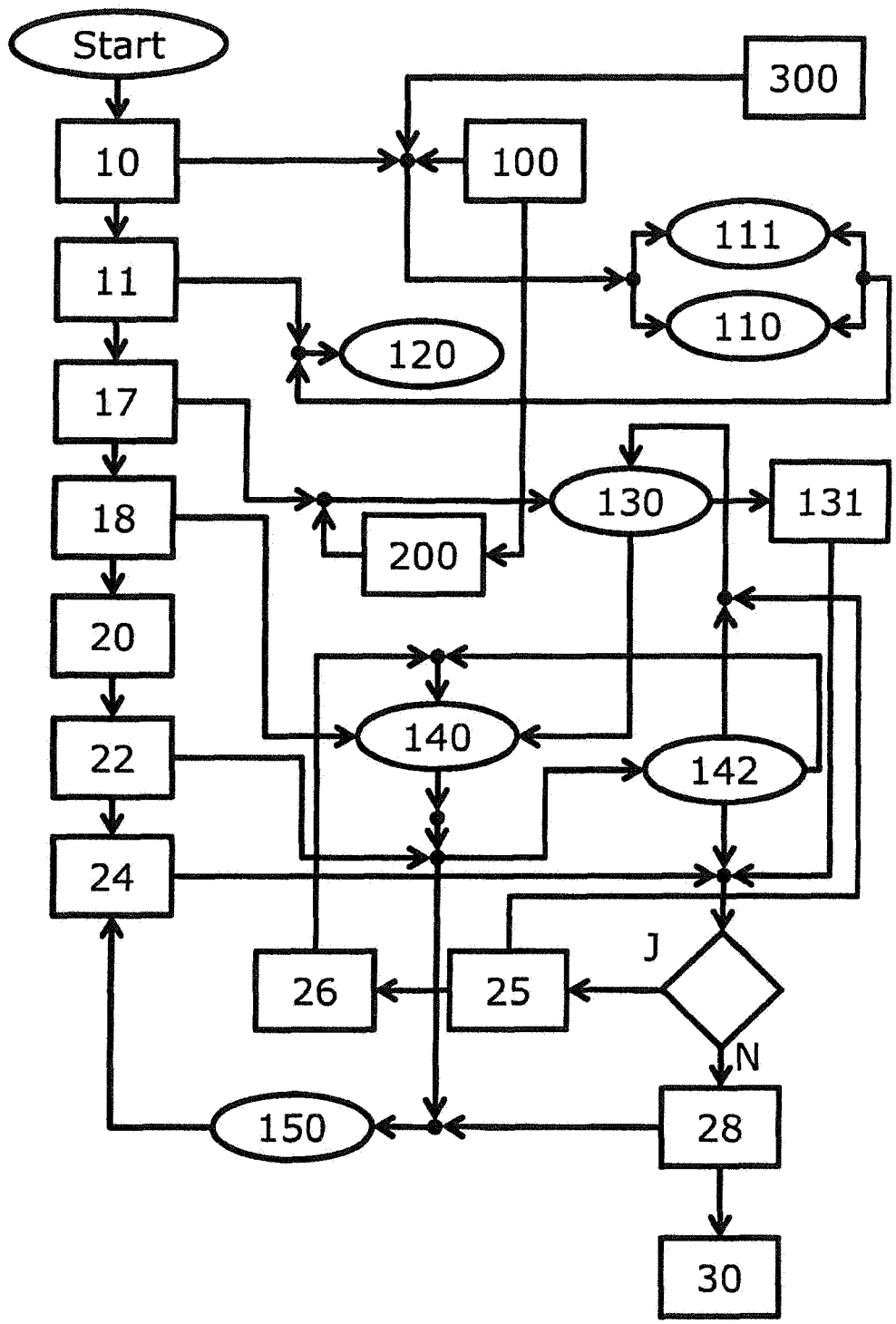
Fig. 1-a

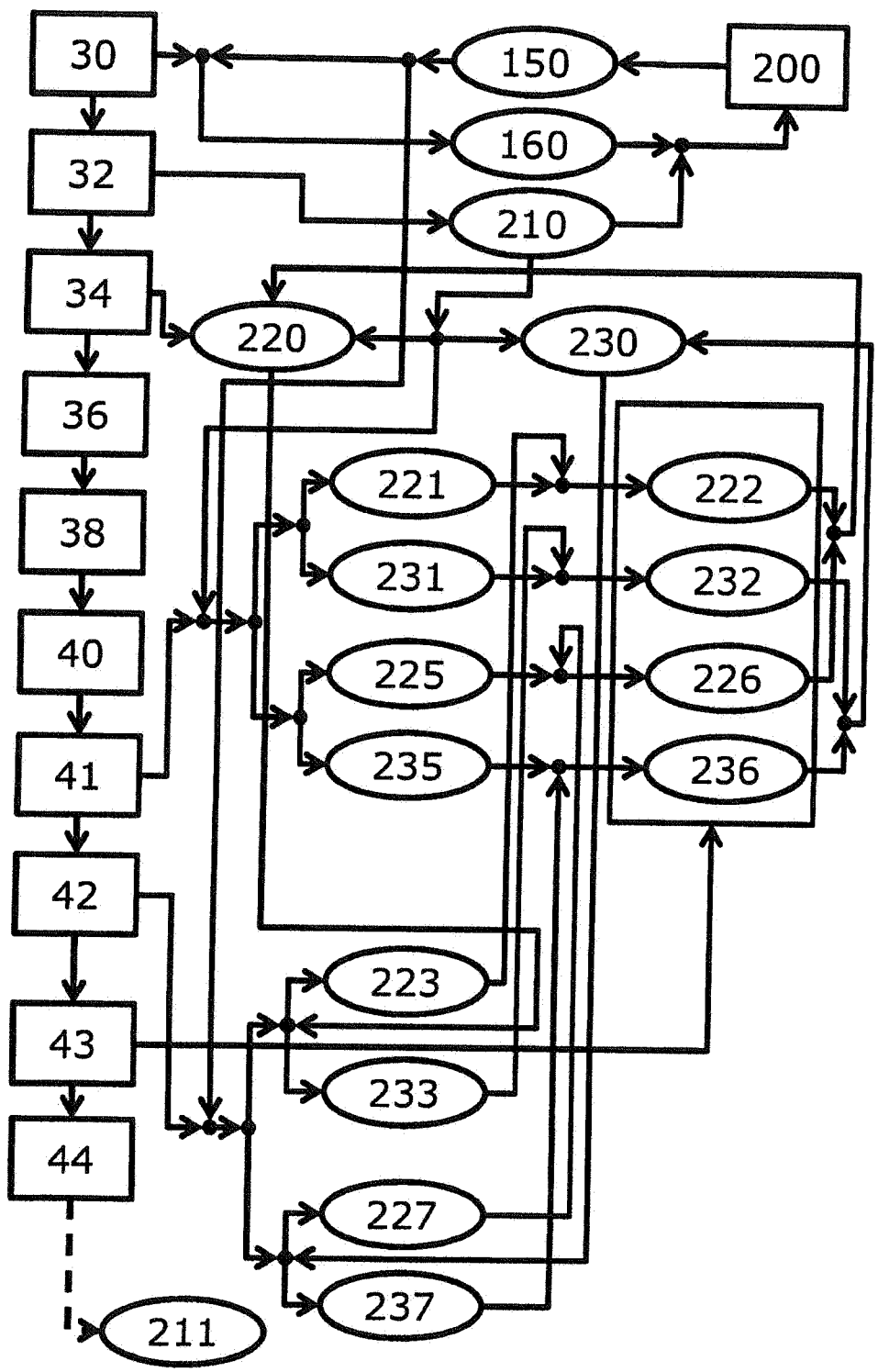
Fig. 1-b

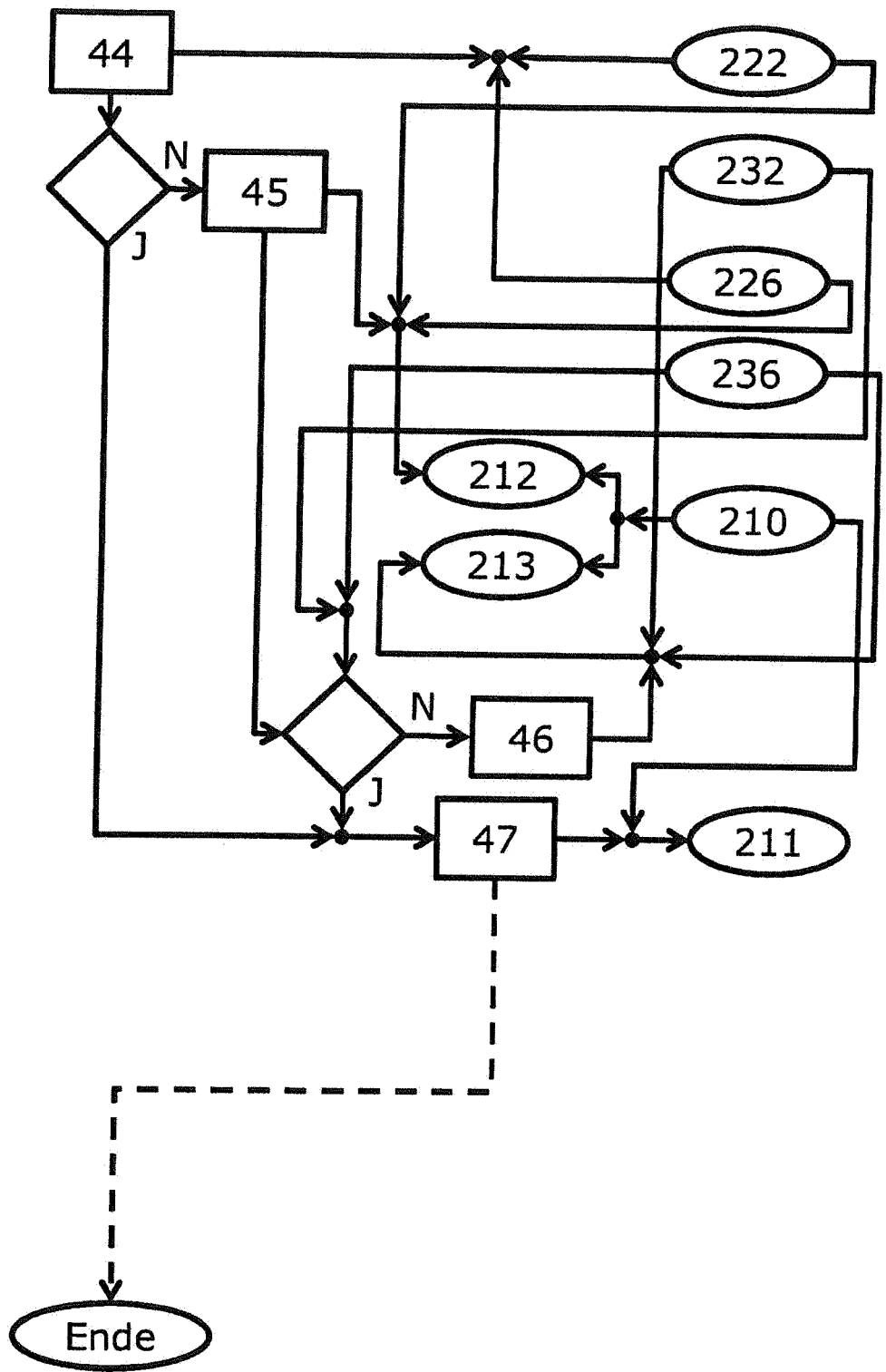
Fig. 1-c

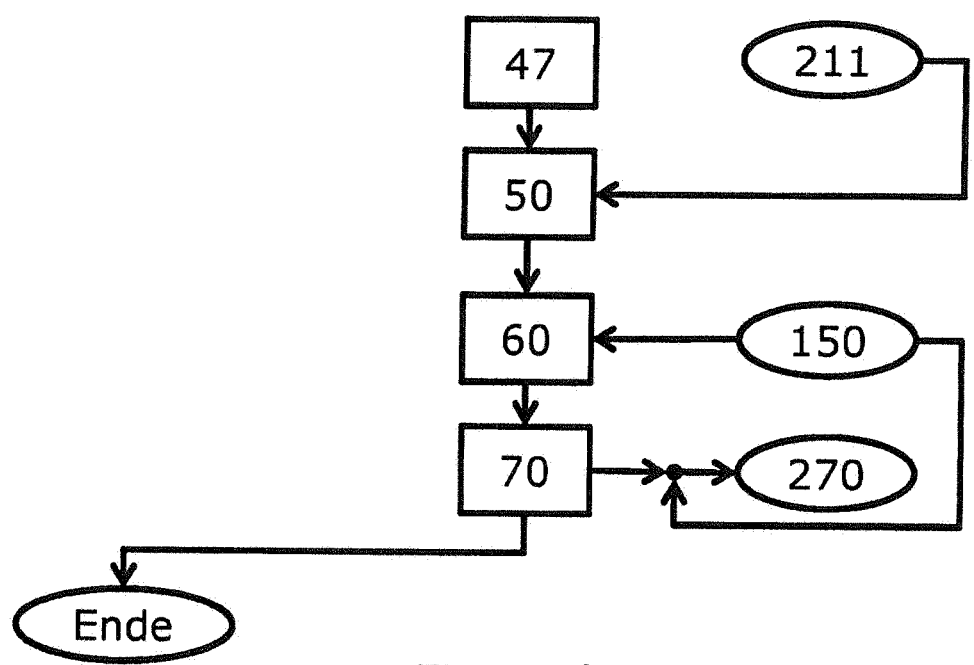
Fig. 1-d

METHOD FOR DETERMINING THE PUPIL DIAMETER OF AN EYE WITH HIGH ACCURACY, AND CORRESPONDING APPARATUS

The present invention relates to a method for highly accurate determining of a pupil diameter of an eye, and a device for this purpose.

BACKGROUND

For a determining of centering data for eyeglasses it is necessary to know the viewing direction of the test person. This can be effected by specification of a fixation object about which further information is known in advance or can be determined, such as, for example, the nasal root method with ImpressionIST, an additional reference object as disclosed in U.S. Pat. No. 7,909,460 B1, or virtually at infinitely distant points.

In addition, the individual data can comprise a position/a diameter of a pupil that is measured in the same situation and is used for optimizing the glasses based on average HOAs, as disclosed in WO 2013/087 212 A1.

However, the common methods detect the pupil quite imprecisely or determine the pupil diameter quite imprecisely.

Furthermore, the measuring of various individual parameters is made possible by different device classes. Thus there are pupillometers for measuring pupil diameters, eye trackers that make possible a viewing-direction measurement, and video-centering systems that determine centering data.

The two first-mentioned device classes are generally used under laboratory conditions, wherein limitations such as head-fixing, absence of ambient light, lack of flexibility due to cable connections, and components to be applied to the test person are accepted. In addition, an absolute measurement is often not necessary, but rather a relative measurement is sufficient, such as, for example a pupil-diameter reaction to light pulses. In addition, with eye tracking, lighting systems are often used whose reflection on the eye is analyzed. For video centering, in determining the pupil diameter the view is usually set to infinity. Since it is usually not possible to attach a fixing object at infinity, devices are required that either image an object at infinity or a correction is performed that, with the view of a known object positioned at a finite distance, can determine the difference to the pupil diameter with the view at infinity. However, an eye model can also be used for this purpose; in particular the eye length is relevant therefor. For this purpose the eye/fixing-object distance is required. With ImpressionIST from Rodenstock, the nasal root of the mirror image of the customer is used as fixing object.

It would therefore be desirable to provide a possibility by which the pupil diameter can be determined with higher precision without requiring information about a fixing object in a video centering, thus making it possible to precisely determine a pupil diameter in an ordinary environment.

It is therefore the goal of the invention to propose a possibility that avoids or at least reduces at least a part of the disadvantages known in the prior art.

BRIEF DESCRIPTION OF THE INVENTION

The object is inventively achieved by a method according to the main claim, as well as by a device according to a further independent claim.

Here the subject matter of the main claim relates to a method for highly accurate determining of a pupil diameter of an eye, using a camera system for spatial capturing of objects, wherein the method includes: image-forming stereoscopic capturing of an eye region of a head, using the camera system, wherein a first and a second stereoscopic image arise for one eye of the eye region. And for each of the two stereoscopic images the method further includes: transferring of the captured eye region of the head into a color space, and continuation of the method in this color space. Determining of a region, within the captured eye region, as a region within a pupil of the eye of the captured eye region, wherein the determined region within the captured eye region exhibits an image criterion wherein the image property represents a largely homogeneous image criterion. Determining a closed outer edge of the region within the pupil. Iterative determining of a closed outer pupil edge, wherein the iterative determining of the outer pupil edge includes: Circumferentially determining, with respect to the outer edge, of a further region outside the edge, along the edge, wherein the further region is adjacent to the closed outer edge of the region within the pupil. Iterative examining of the further region as to whether the further region exhibits the image criterion. And if at least a part of the further region exhibits the image criterion, an integration occurs of those parts of the further region, which have the image criterion, in the region within the pupil of the eye, and an expanding occurs of the closed outer edge of the region inside the pupil to the integrated part of the further region. And if the further region does not completely have the image criterion, an establishing occurs of the closed outer edge of the region inside the pupil as the outer edge of the pupil of the eye. For each of the two stereoscopic images the method further includes: Determining of a third region as pupil of the eye, wherein the third region is that region that is completely enclosed by the outer edge of the pupil.

In one embodiment the method further includes: Determining of a point in the pupil. Determining of a first straight line through the point. Determining of a second straight line through the point, wherein the second straight line is disposed orthogonal to the first straight line. And iterative determining of a pupil center point, wherein the iterative determining of the pupil center point includes: Determining of a first segment and of a second segment for each straight line, wherein the determining of the respective segment includes: Determining of a first endpoint of the corresponding segment, wherein the first endpoint corresponds to the point in the pupil. Determining of a second endpoint of the corresponding segment, wherein the second endpoint corresponds to an intersection of the corresponding straight line with the edge of the pupil. And determining of the corresponding segment as a line along the corresponding straight line starting from the corresponding first endpoint leading to the corresponding second endpoint. Furthermore, the iterative determining of the pupil center point includes: Iterative comparison of length of the two segments of the first straight line. If the two segments of the first straight line are not equal in length, an incrementing occurs of a first coordinate of the point in the pupil, along the longer of the two segments of the first straight line. If the two segments of the second straight line are not equal in length, an incrementing occurs of a second coordinate of the point in the pupil, which incrementing occurs along the longer of the two segments of the second straight line. And if the two segments of the first straight line are equal in length and the two segments of the second straight line are equal in length, an establishing occurs of the point in the pupil as the pupil center point of the pupil of the eye.

In one embodiment the method further includes: Triangulated superposing of the two center points of the pupil of the eye of the two stereoscopic images. Triangulated superposing of the two outer edges of the pupil of the eye of the two stereoscopic images. And determining of the pupil diameter based on the two triangulated superpositions.

Here the method steps can each be carried out automatically.

Here an eye region in the sense of the invention means the region of the face wherein both eyes lie.

Here an image criterion in the sense of the invention can be a property of an image, as is used for technical image description. Such image properties can be, for example, a histogram, saturation, contrast, and the like. The image criterion can thus be dependent on the color space used itself.

A largely homogeneous image criterion in the sense of the invention means that the corresponding image property exhibits homogeneity at least in a significantly large region of the image. With regard to a pupil, such a largely homogeneous region within the determined region within the captured eye region can include at least a part of the total pupil surface, for example, at least 10% of the pupil surface, preferably at least 5% of the pupil surface.

Based on a stereo camera system, an image is recorded of a partial region of a head such that the eye region is visible in both images.

Deviating therefrom, instead of the horizontal alignment, an alignment of the optical axis about a known angle can also occur, and this alignment can subsequently be taken into account for the video centering.

In both images the pupil, preferably the pupil center, is selected.

For the automatic variant, image-processing methods are used that can demand trained models and/or the structure information in the image.

Based on this information a localization of the pupil in the space is already possible. It is thus implicitly possible to calculate a scaling factor of image pixels to a length unit at this position.

The environment of the image at the selected pupil position can be modified by a pre-processing.

In addition it is taken advantage of that the pupil is the darkest object. This can be used, for example, in order to establish a lower threshold value, below which the brightness can be set to a fixed, identical value. Thus the information that is present in the pupil can be treated as an artifact and thus removed.

An incrementing of the corresponding coordinates of the point in the pupil, along the longer of the two segments of the corresponding straight line in the sense of the invention, means here, for example, that the two segments can be summed and then the corresponding coordinate along the longer segment is displaced by the amount that the shorter segment lacks with respect to the length of half of the summed segments. However, the incrementing can also occur pixel-by-pixel or by a fixed value or also by a percentage of the length of the longer segment.

Due to the inventive teaching the advantage is achieved that complex instrument constructions can be omitted, and the pupil diameter can be measured in natural usage situations. A further advantage is that a method is provided for an accurate determining of the pupil diameter, which method can be used for a brightness-dependent adapting of an eyeglass lens.

Here the subject matter of a further independent claim relates to a device for highly accurate determining of a pupil diameter of an eye. Here the device includes: A camera system for spatial capturing of objects. A capturing means for imaging stereoscopic capturing of an eye region of a head, using the camera system, for generating a first and a second stereoscopic image for an eye of the eye region. A transferring means for transferring of the captured eye region of the head into a color space. A first determining means for determining of a region, within the captured eye region, as a region within a pupil of the eye of the captured eye region. A second determining means for determining of a closed outer edge of the region within the pupil. A third determining means for iterative determining of a closed outer pupil edge.

In one embodiment the device further includes: A first determining means for determining of a point in the pupil. A second determining means for determining of a first straight line through the point. A third determining means for determining of a second straight line, disposed orthogonal to the first straight line, through the point. A fourth determining means for iterative determining of a pupil center point.

In one embodiment the device further includes: A first triangulating means for triangulated superposing of the pupil center points of the pupil of the eye of the stereoscopic images. A second triangulating means for triangulated superposing of the outer edges of the pupil of the eye of the stereoscopic images. And a fifth determining means for determining of the pupil diameter based on the two triangulated superpositions. And here the device is configured to perform any inventive method.

Due to the inventive teaching the advantage is achieved that a device can be provided using which the pupil diameter can be measured in natural usage situations. A further advantage is that a method is provided for an accurate determining of the pupil diameter, which method can be used for a brightness-dependent adapting of an eyeglass lens.

Here the subject matter of a further independent claim relates to a computer program product for a device, wherein the device is operable according to any inventive method.

Due to the inventive teaching the advantage is achieved that the method can be carried out automatically in a particularly efficient manner.

Here the subject matter of a further independent claim relates to a data carrier including an inventive computer program product.

Due to the inventive teaching the advantage is achieved that the method can be distributed or retained in a particularly efficient manner on the devices, systems, and/or motor vehicles carrying out the method.

Before designs of the invention are described in more detail below, it is first to be stipulated that the invention is not limited to the described components or the described method steps. Furthermore, the terminology used also does not represent any limitation, but rather has only illustrative character. To the extent that the singular is used in the description and the claims, the plural is respectively included provided the context does not explicitly exclude this. Any method steps can be carried out automatically provided the context does not explicitly exclude this. Corresponding method sections can lead to corresponding device properties and vice versa, so that a change of a method feature into a device feature is made possible and vice versa, provided the context does not explicitly exclude this.

Further exemplary designs of the inventive method are explained below.

According to a first exemplary design the method further includes a calibrating of the camera system for the spatial capturing of objects prior to the imaging stereoscopic capturing of the eye region of the head. Here the calibrating preferably occurs based on a predefined angle and/or a predefined distance of the camera system to a reference object. And here during the stereoscopic capturing the head of the eye region to be captured is located at the position of the reference object.

This design has the advantage that the pupil diameter can thus be determined even more precisely.

According to a further exemplary design the method further includes a determining of an eye in the stereoscopically captured eye region, based on a comparison of the stereoscopically captured eye region to an eye model.

This design has the advantage that an eye can be independently determined, whereby the pupil-diameter determining can be simplified still further.

According to a further exemplary design the method further includes that the color space corresponds to a color space wherein the image criterion is determined in a particularly suitable manner.

If the image is recorded, for example, using an RGB sensor, a color-space transformation can be carried out. Since the color of the iris can be different, the RGB color space is not well suited to detect brightness differences. The CIELAB color space is better suited, for example, wherein, for example, only the X channel is then considered.

This design has the advantage that the edge of the pupil can thus be determined even more precisely.

According to a further exemplary design the method further includes that the image criterion includes a contrast criterion.

This design has the advantage that the edge of the pupil can thus be determined even more precisely.

According to a further exemplary design the method further includes that the color space corresponds to a CIELAB color space.

This design has the advantage that the edge of the pupil can thus be determined even more precisely.

According to a further exemplary design the method further includes that the determining of the region within the captured eye region, as the region within the pupil of the eye of the captured eye region, occurs based on a pupil criterion, preferably based on a comparison to a pupil model.

This design has the advantage that the pupil can be determined more simply.

According to a further exemplary design the method further includes: Determining a further point in the pupil. Determining a further straight line through the further point. Determining a further second straight line through the further point, wherein the further second straight line is disposed orthogonal to the further first straight line. And here the iterative determining of the pupil center point further includes: Determining a further first segment and a further second segment for each further straight line, wherein the determining of the respective segment includes: Determining a further first endpoint of the corresponding segment, wherein the first further endpoint corresponds to a further point in the pupil. Determining a further second endpoint of the further corresponding segment, wherein the further second endpoint corresponds to an intersection of the corresponding further straight line with the edge of the pupil. And determining the corresponding further segment as a line along the corresponding further straight line starting from the corresponding further first endpoint leading to the corresponding further second endpoint. And the iterative determining of the pupil center point further includes: comparing of length of the two further segments of the further first straight line. If the two further segments of the further first straight line are not equal in length, an incrementing occurs of a further first coordinate of the further point in the pupil, which incrementing occurs along the longer of the two further segments of the further first straight line. If the two further segments of the further second straight line are not equal in length, an incrementing occurs of a further second coordinate of the further point in the pupil, which incrementing occurs along the longer of the two further segments of the further second straight line. And if the two further segments of the further first straight line are equal in length and the two further segments of the second further straight line are equal in length, an establishing occurs of the further point in the pupil as a further center point of the pupil of the eye.

This can be useful when, for example, using an object-recognition method the surface of the pupil has been recognized as not circular, but rather elliptical, and thus two points function as center points. In order to be able to accurately determine these two center points, mathematically more complex processes may be required as are necessary for determining foci of an ellipse. Here the connecting lines from a point along the ellipse to the two foci lie mirror-inverted with respect to normals to the ellipse at this point.

This design has the advantage that the pupil diameter is determinable with high precision even with highly elliptical pupil images or highly elliptical pupils.

According to a further exemplary design the method further includes: Triangulated superposing of the further two center points of the pupil of the eye of the two stereoscopic images. Triangulated superposing of the two outer edges of the pupil of the eye of the two stereoscopic images. And determining of the further pupil diameter based on the two triangulated superpositions.

This design has the advantage that the pupil diameter can be determined even more precisely.

According to a further exemplary design the method further includes a determining of a scale based on a distance of the camera system to the stereoscopically captured eye region of the head and a pixel criterion of the camera system. And here the determining of the respective pupil diameter occurs based on the determined scale.

This design has the advantage that the pupil diameter can be determined even more precisely.

According to a further exemplary design the method further includes that the pixel criterion of the camera system includes a pixel size or pixel width and a pixel count.

This design has the advantage that the pupil diameter can be determined even more precisely.

According to a further exemplary design the method further includes, prior to the determining of the region within the captured eye region, as the region within the pupil of the eye of the captured eye region: Examining of the captured eye region for reflections. And if the captured eye region includes at least one reflection, the method further includes a removing of the appearing reflection using a vicinity criterion such that image information in a region wherein the reflection appears is replaced by corresponding image information of the corresponding neighboring pixels based on the vicinity criterion.

Relevant steps here are the detection of illumination reflections wherein a high brightness occurs or the image is oversaturated, within the pupil and in particular at the edge of the pupil.

These regions are overwritten by image information from the environment, so-called "inpainting," for example, using a "next/closest neighbor" method.

This design has the advantage that the edge of the pupil is even more precisely determinable.

According to a further exemplary design the method further includes: Carrying out of the method for a first eye of the stereoscopically captured eye region. And performing of the method for a second eye of the stereoscopically captured eye region.

This design further has the advantage that the pupil diameter can be precisely determined for both eyes in one step. The pupil-diameter determining can thereby be carried out for both eyes using the same image.

Furthermore it can also be taken advantage of that the pupils have no structure, however, the iris typically has structure. This difference can also be taken advantage of by the calculating of the local entropy of the image.

Furthermore, a correspondingly pre-processed image can be transformed into polar coordinates using a selected pupil center point as origin. A circular dark-light transition thereby appears as a line. An ellipse would be imaged as a sine/cosine curve. In this transformed image a dark-light edge can now be sought. This can be effected using conventional edge filters, such as, for example, Canny, Sobel, and the like. The coordinate of the determined edge then corresponds to the average radius of the pupil in pixels.

The conversion of pixels into a length unit can be performed using a scaling factor that results from the triangulation.

A still more accurate center-determining, pupil-shape can occur as follows:

Instead of detecting the dark-light edge over the entire angle range, this can also occur in segments. With a use of, for example, four segments, it is possible to determine a deviation of the selected pupil center point from the actual center point when opposing segments have differences in the determined radii. It is then possible to use this difference for repositioning of the pupil center point. A checking is easily possible by further application of the method. Preferably an adjustment of the center point smaller than half of the difference is performed and repeatedly checked until the difference has fallen below an established threshold value and thus the exact pupil center point is determined.

Moreover, with more than four segments, a detection of more complex forms, such as, for example, an ellipse, is possible, or with even more segments a different parameterization of the pupil shape, such as, for example, as an n-ellipse or as a spline and the like.

The ellipse is expected in the image as the shape of an ideal, circular pupil, since the pupil plane generally is not parallel to the image plane of the recording camera or cannot be parallel to both image planes. Their detection means thus means an improvement of the accuracy with respect to the pupil diameter.

Furthermore, a comparison between the two images of the stereo camera system is advantageous, since a comparison can be performed between these in order to check the plausibility of the pupil shape found.

From the radii segments, points can be selected at the pupil-to-iris transition in both images. These can be combined via triangulation into a point in the space. If three or more segments are used, the pupil plane can be determined therefrom. The optical axis of the eye and the viewing direction can be assumed to be perpendicular to this plane or to have a known, fixed angle. The determining of the viewing direction is thus possible therefrom.

Preferably considerably more than three points can be used for the plane-determining. Here 4, 6, 8, 12, 16, 24, 32 or 64 segments are available.

To check the 3D contour of the pupil-iris transition or of the pupil shape, the Sampson distance, i.e., a first-order approximation, can be calculated for the geometric error for the points to be triangulated. If this has an unusually high value for a point pair, then an error detection is assumed here instead of a deviation from the circle/ellipse shape. For this point pair it can either be attempted again to carry out a detecting using modified parameters or the point pair is discarded.

A fixing point can be determined from the viewing direction of a right and of a left eye. This can be, for example, the point at which the two straight lines that describe the viewing direction have the smallest distance to each other. The fixing point is known in the world coordinate system wherein the other points are also known.

The determining of a reading distance would thus also be possible without corresponding devices.

Using a device that includes a stereo camera system the invention thus allows simultaneous images, using the two cameras, in normal usage and environment situations, of a test person, which images include the eye region of the test person. 3D position data of selected object points can be very precisely determined from these images by a known calibration of the cameras.

In the present invention a pupil edge is first determined in the individual images. This can occur stepwise, for example, first face or eye region, then eye, then pupil center point, then pupil edge, and semi-automatically or fully automatically here. Here the pupil edge indicates the predominantly round shape that describes the transition between pupil and iris of an eye. Due to the perspective view an ideally circular pupil would be depicted as an ellipse. Further deviations from a circular shape result in further perspective distortions. After successful determining of the pupil edges in both images, i.e., each in 2D, the 3D position and shape of the pupil edge is determined.

It can be at least approximately assumed therefrom that the normal to the surface that is described by the pupil edge corresponds to the viewing direction. The viewing direction can thus be determined.

If the determining of the viewing direction occurs for both eyes, a possible intersection of the two viewing directions can be determined. In general the viewing directions of the two eyes do not exactly intersect. The intersection point can be determined, for example, as the point that has the smallest distance of the viewing directions or as the intersection in a projection along a straight line that extends centrally through the two pupils, i.e., is predominantly perpendicular; the projection thus occurs in a horizontal plane. The distance of the intersection to the pupil position can thus be used for determining an object distance.

The 3D position and shape of the pupil edge can be used to determine a precise pupil diameter or radius therefrom. Here the shape in its 2D projection is approximated to a circle whose radius is then used as pupil radius. Diverse compensation methods are described in the literature both for the projection in 2D and for the circle-fitting. The adjustment is possible, for example, using a target function that is to be minimized. The target function can describe, for example, the sum of squares of distances between measured points and approximated points.

Since the object distance can be determined without a fixing object being necessary, any viewing situation can be measured. This is helpful, for example, for determining distances that are used in a user-specific manner with the use of certain devices, such as, for example, monitors at the workplace, hand-held input/output devices such as smartphones, tablets, test devices including displays, display instruments in a cockpit and the like, or also other predominantly static activity-specific distances, such as, for example, reading books, playing golf, handwork, cycling, and the like. Dynamic situations can be statistically imaged over a plurality of measurements.

Under certain circumstances not all individual parameters can be determined with such an individual measurement. This includes, for example, forward tilt that is dependent on the position of the optical axes of the recording cameras. However, these data can be completed by a comparison with a data set under correspondingly defined conditions. For example, a first measurement could be carried out with horizontal first optical axis, and a second measurement in an application situation, for example, as with handwork at the table, with bent head. Via the centering data and object distances determinable in the second measurement, together with the first measurement a complete data set including two pieces of object distance information relative to a point in the flat plane is available. Alternatively a correction of the angle of the first optical axis is also possible when it is determined by an additional device at the time of the recording.

Alternatively the determining of the intersection of the viewing directions can also be used to check the compliance of a predetermined viewing task with fixation of a defined object. Thus with use of the nasal root method the distance of the nasal root in the mirror image can be determined and compared with the distance through the intersection points. With too-large deviations the measurement can be invalidated or an indication can be given to the operator, whereupon the operator can check the fixation of the test person and optionally correct it.

Using the method described here complex instrument devices can thus be omitted, since the distance to the fixing object can be determined and thus no cooperation of the customer is required.

BRIEF DESCRIPTION OF THE FIGURES

The invention shall be explained in more detail below with reference to the Figures.

FIG. 1 shows a schematic illustration of a proposed method according to an exemplary design of the invention;

DETAILED DESCRIPTION

Figure 2:
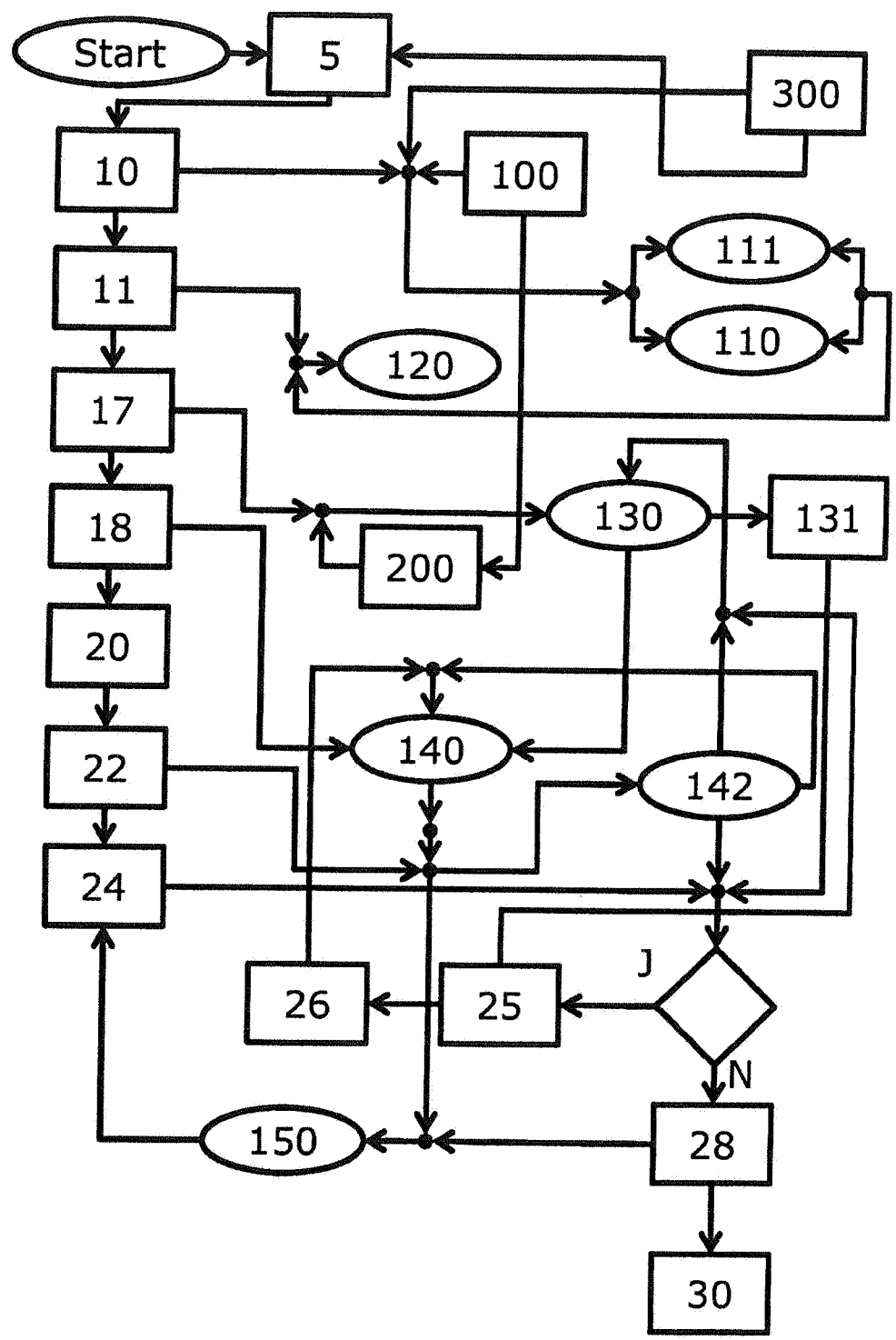
FIG. 2 shows a schematic illustration of a proposed method according to a further exemplary design of the invention.

In the following the invention shall be depicted in more detail (with reference to the Figures). It is to be noted here that different aspects are described that can each be used individually or in combination. That is, any aspect can be used with different embodiments of the invention if not explicitly depicted as a pure alternative. Furthermore, in the following, for the sake of simplicity, only one entity is generally referred to. Unless explicitly indicated, however, the invention can respectively include a plurality of the entities concerned. In this respect the use of the words "a," "an," and "of a" are understood only as an indication that at least one entity is used in a simple embodiment.

Insofar as methods are described below, the individual steps of a method can be arranged and/or combined in any sequence provided something deviating does not explicitly result due to the combination. Furthermore—unless expressly indicated otherwise—the methods can be combined with one another.

Data including numerical values are generally not to be understood as exact values, but rather also include a tolerance of +/−1% up to +/−10%.

References to standards or specifications or norms are to be understood as references to standards or specifications or norms that apply/applied at the time of the application and/or—if a priority is claimed—the time of the priority application. However, no general exclusion of the applicability of subsequent or replacement standards or specifications or norms is to be understood thereby.

In the following, "neighboring" explicitly implies a direct-vicinity relationship, without, however, being limited thereto. In the following, "between" explicitly implies a position wherein the intermediate part has a direct vicinity to the surrounding parts.

FIG. 1 shows a schematic illustration of a proposed method according to an exemplary design of the invention.

Here FIG. 1 shows a schematic illustration of a method for highly accurate determining of a pupil diameter 270 of an eye, using a camera system 300 for spatial capturing of objects. Here the method includes:

(FIG. 1-*a*):

Imaging stereoscopic capturing 10 of an eye region 100 of a head, using the camera system 300, wherein a first and a second stereoscopic image 110, 111 arise for an eye of the eye region 100. And for each of the two stereoscopic images 110, 111 the method further includes: transferring 11 of the captured eye region 100 of the head into a color space 120, and continuing of the method in this color space 120. Determining 17 of a region 130 within the captured eye region 100, as a region 130 within a pupil 200 of the eye of the captured eye region 100, wherein the determined region 130 within the captured eye region 100 has an image criterion 131. Here the image criterion 131 represents a largely homogeneous image criterion. Determining 18 of a closed outer edge 140 of the region 130 within the pupil 200. Iterative determining 20 of a closed outer pupil edge 150, the iterative determining 20 of the outer pupil edge 150 including: Circumferentially determining 22, with respect to the outer edge 140, of a further region 142, outside the edge 140, along the edge 140, wherein the further region 142 is adjacent to the closed outer edge 140 of the region 130 inside the pupil 200. Iterative examining 24 of the further region 142 as to whether the further region 142 has the image criterion 131. And if at least a part of the further region 142 has the image criterion 131: Integrating 25 of the part of the further region 142, which has the image criterion 131, in the region 130 within the pupil 200 of the eye. Expanding 26 of the closed outer edge 140 of the region 130 within the pupil 200 to the integrated part of the further region 142. And if the further region 132 does not completely have the image criterion 131: Establishing 28 of the closed outer edge 140 of the region 130 within the pupil 200 as the outer edge 150 of the pupil 200 of the eye.

FIG. 1-*b*:

And determining 30 of a third region 160 as pupil 200 of the eye, wherein the third region 160 is the region that is completely enclosed by the outer edge 150 of the pupil 200.

In embodiments of the invention, the following can be performed: Determining 32 of a point 210 in the pupil 200. Determining 34 of a first straight line 220 through the point 210. Determining 36 of a second straight line 230 through the point 200, wherein the second straight line 230 is disposed orthogonal to the first straight line 220. And iterative determining 38 of a pupil center point 211, wherein the iterative determining 38 of the pupil center point 211 includes: Determining 40 of a first segment 222, 232 and a second segment 226, 236 for each straight line 220, 230, wherein the determining 40 of the respective segment 222, 232, 226, 236 includes: Determining 41 of a first endpoint 221, 231, 225, 235 of the corresponding segment 222, 232, 226, 236, wherein the first endpoint 221, 231, 225, 235 corresponds to the point 210 in the pupil 200. Determining 42 of a second endpoint 223, 233, 227, 237 of the corresponding segment 222, 232, 226, 236, wherein the second endpoint 223, 233, 227, 237 corresponds to an intersection of the corresponding straight line 220, 230 with the edge of the pupil 150. And determining 43 of the corresponding segment 222, 232, 226, 236 as a line along the corresponding straight line 220, 230 starting from the corresponding first endpoint 221, 231, 225, 235 leading to the corresponding second endpoint 223, 233, 227, 237.

FIG. 1-*c*:

Iterative comparing 44 of lengths of the two segments 222, 226 of the first straight line 220. And if the two segments 222, 226 of the first straight line 220 are not equal in length: Incrementing 45 of a first coordinate of the point 210 in the pupil 200, along the longer of the two segments 222, 226 of the first straight line 220. And if the two segments 232, 236 of the second straight line 230 are not equal in length: Incrementing 46 of a second coordinate 213 of the point in the pupil 200, along the longer of the two segments 232, 236 of the second straight line 230. And if the two segments 222, 226 of the first straight line 220 are equal in length, and the two segments 232, 236 of the second straight line 230 are equal in length: Establishing 47 of the point 210 in the pupil 200 as the pupil center point 211 of the pupil 200 of the eye.

(FIG. 1-*d*):

In embodiments of the invention, the following can then be performed: Triangulated superposing 50 of the two center points 211 of the pupil 200 of the eye of the two stereoscopic images 110, 111. Triangulated superposing 60 of the two outer edges 150 of the pupil 200 of the eye of the two stereoscopic images 110, 111. And determining 70 of the pupil diameter 270, based on the two triangulated superpositions 50, 60.

FIG. 2 shows a schematic illustration of a proposed method according to a further exemplary design of the invention.

Here FIG. 2 shows a schematic illustration of a method further developed with respect to FIG. 1 or FIG. 1-*a*. The above-mentioned for FIG. 1 therefore continues to also apply for FIG. 2.

Here FIG. 2 shows a schematic illustration of a proposed method wherein the method includes, in addition to the method section of FIG. 1-*a*: Calibrating 5 of the camera system 300 for spatial capturing of objects, before the imaging stereoscopic capturing 10 of the eye region 100 of the head. Here the calibrating 5 preferably occurs based on a predefined angle and/or a predefined distance of the camera system 300 to a reference object. And here, during the stereoscopic capturing, 10 the head of the eye region 100 to be captured is located at the position of the reference object.

Figure 3:
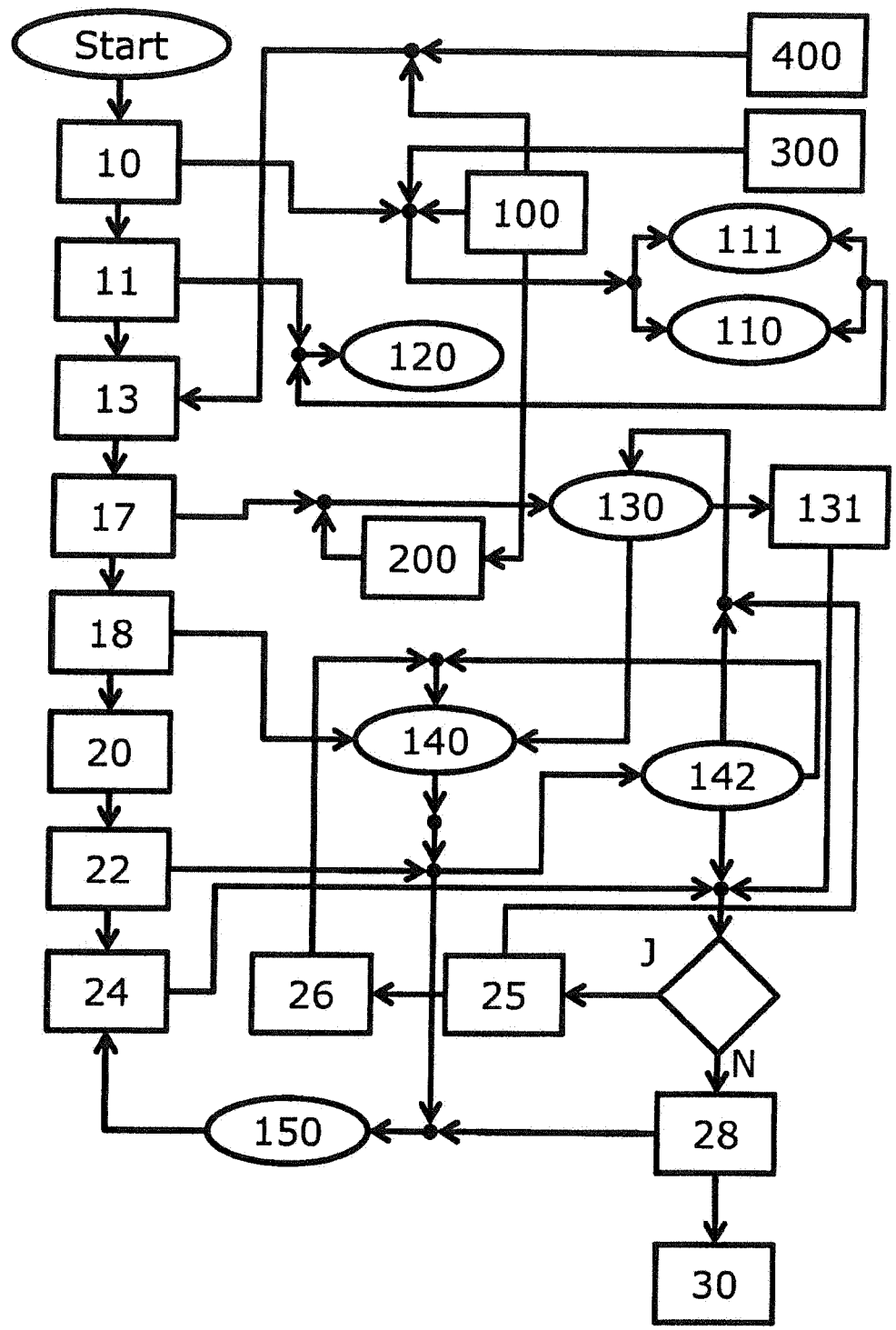
FIG. 3 shows a schematic illustration of a proposed method according to a further exemplary design of the invention.

FIG. 3 shows a schematic illustration of a proposed method according to a further exemplary design of the invention.

Here FIG. 3 shows a schematic illustration of a method further developed with respect to FIG. 1 and FIG. 2. The above-mentioned for FIGS. 1 and 2 therefore continues to also apply for FIG. 3.

Here FIG. 3 shows a schematic illustration of a proposed method, wherein the method further includes a determining 13 of an eye in the stereoscopically captured 10 eye region 100 based on a comparison of the stereoscopically captured 10 eye region 100 with an eye model 400.

Figure 4:
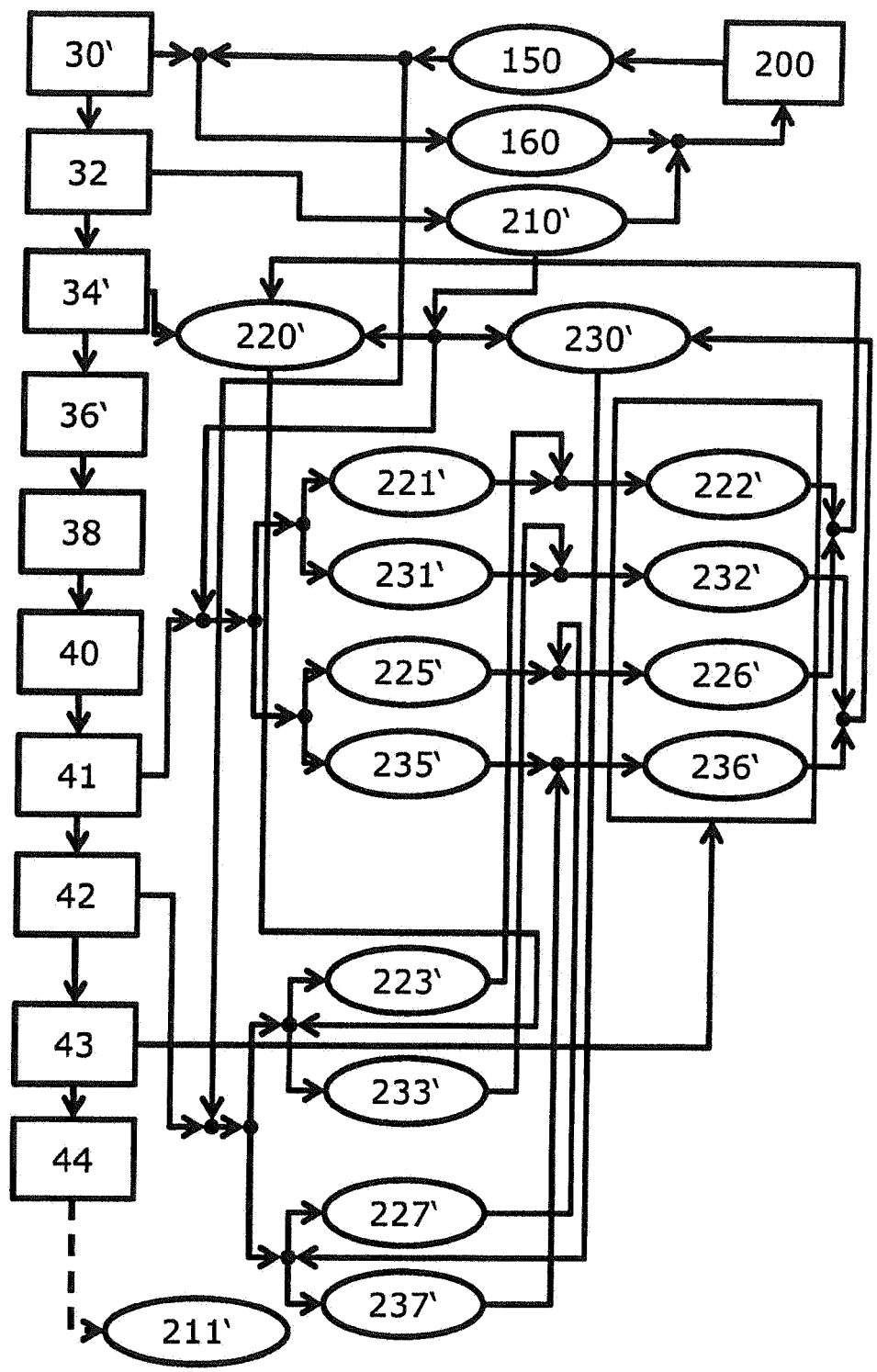
FIG. 4 shows a schematic illustration of a proposed method according to a further exemplary design of the invention.

FIG. 4 shows a schematic illustration of a proposed method according to a further exemplary design of the invention.

Here FIG. 4 shows a schematic illustration of a method further developed with respect to FIG. 1 to FIG. 3. The above-mentioned for FIGS. 1 to 3 therefore continues to also apply for FIG. 4.

Here FIG. 4 shows a schematic illustration of a proposed method, wherein the method further includes: Determining 32' of a further point 210' in the pupil 200. Determining 34' of a further first straight line 220' through the further point 210'. Determining 36' of a further second straight line 230' through the further point 210', wherein the further second straight line 230' is disposed orthogonal to the further first straight line 220'. And here the iterative determining 38 of the pupil center point 211 further occurs respectively in accordance with the further point 210', the further first straight line 220', and the further second straight line 230'. And as a result a corresponding establishing occurs of the further point 210' in the pupil 200, as a further center point 211' of the pupil 200 of the eye.

Here the reference numbers including apostrophes indicate respectively associated references of the further point 210' in analogy to the associated references of the point 210.

Figure 5:
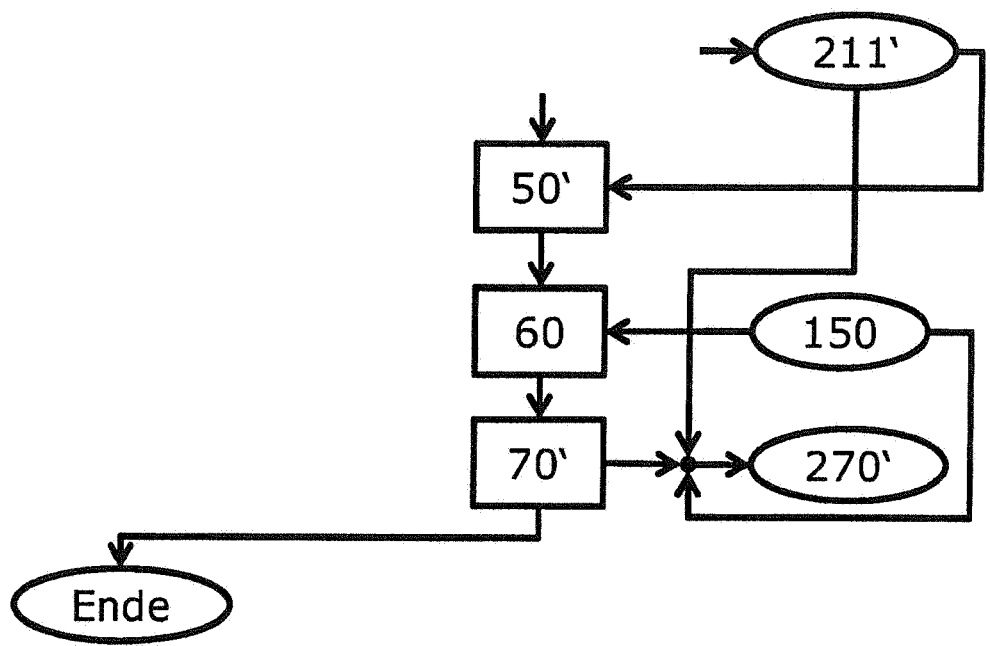
FIG. 5 shows a schematic illustration of a proposed method according to a further exemplary design of the invention.

FIG. 5 shows a schematic illustration of a proposed method according to a further exemplary design of the invention.

Here FIG. 5 shows a schematic illustration of a method further developed with respect to FIG. 4. The above-mentioned for FIG. 4 therefore continues to also apply for FIG. 5.

Here FIG. 5 shows a schematic illustration of a proposed method, wherein the method further includes: Triangulated 50' superposing of the further two center points 211' of the pupil 200 of the eye of the two stereoscopic images 110, 111. And determining 70' of the further pupil diameter 270' based on the two triangulated superpositions 50', 60.

Figure 6:
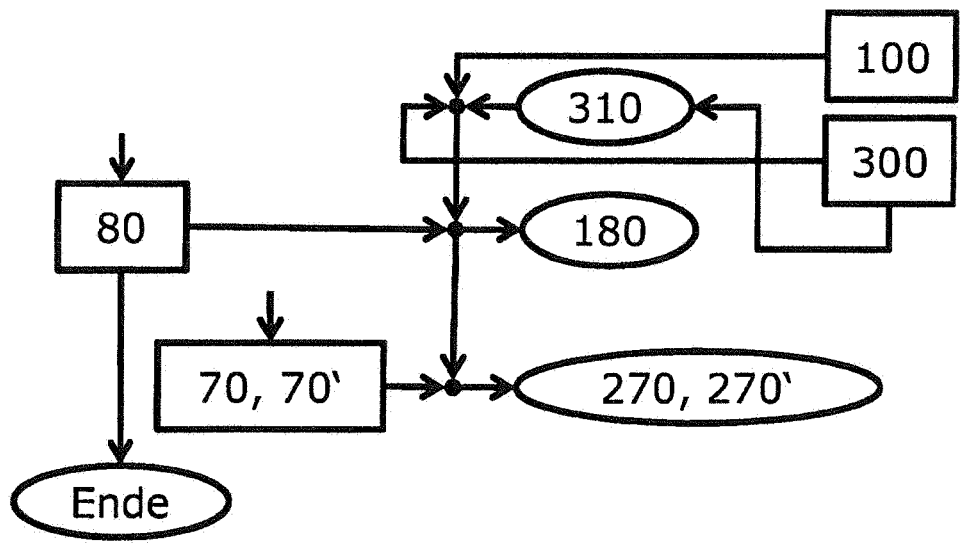
FIG. 6 shows a schematic illustration of a proposed method according to a further exemplary design of the invention.

FIG. 6 shows a schematic illustration of a proposed method according to a further exemplary design of the invention.

Here FIG. 6 shows a schematic illustration of a method further developed with respect to FIG. 1 to FIG. 5. The above-mentioned for FIGS. 1 to 5 therefore continues to also apply for FIG. 6.

Here FIG. 6 shows a schematic illustration of a proposed method, wherein the method further includes a determining 80 of a scale 180, based on a distance of the camera system 300 to the stereoscopically captured eye region of the head and of a pixel criterion 310 of the camera system 300. And here the determining 70, 70' of the respective pupil diameter 270, 270' is effected based on the determined scale 180.

Figure 7:
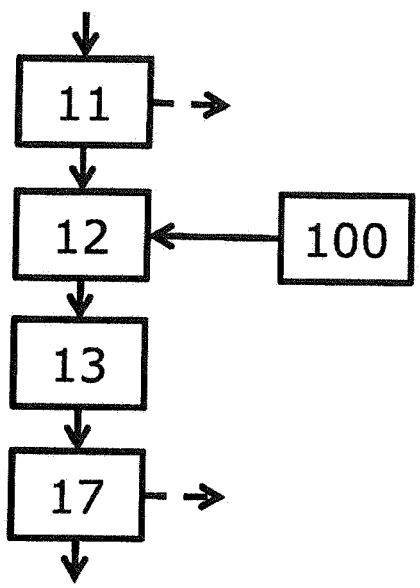
FIG. 7 shows a schematic illustration of a proposed method according to a further exemplary design of the invention.

FIG. 7 shows a schematic illustration of a proposed method according to a further exemplary design of the invention.

Here FIG. 7 shows a schematic illustration of a method further developed with respect to FIG. 1 to FIG. 6. The above-mentioned for FIGS. 1 to 6 therefore continues to also apply for FIG. 7.

Here FIG. 7 shows a schematic illustration of a proposed method, wherein the method further includes, before the determining 17 of the region 130 within the captured eye region 100, as the region 130 within the pupil 200 of the eye of the captured eye region 100: Examining 12 of the captured eye region 100 for reflections. And if the captured eye region 100 includes at least one reflection: Removal 13 of the appearing reflection or reflections using a vicinity criterion such that image information in a region wherein the reflection occurs is replaced by corresponding image information of the corresponding neighboring pixels based on the vicinity criterion.

Figure 8:
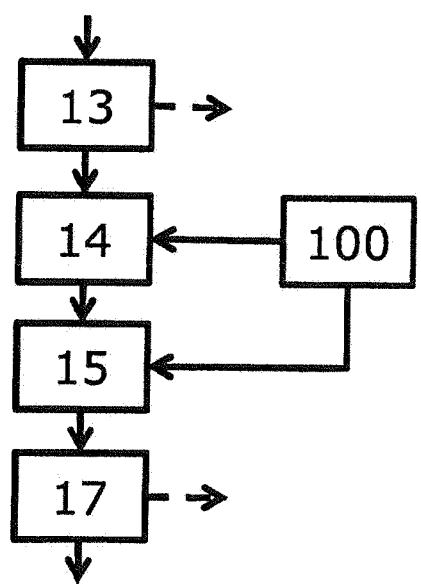
FIG. 8 shows a schematic illustration of a proposed method according to a further exemplary design of the invention.

FIG. 8 shows a schematic illustration of a proposed method according to a further exemplary design of the invention.

Here FIG. 8 shows a schematic illustration of a proposed method, wherein the method further includes a performing of the method 14 for a first eye of the stereoscopically captured eye region 100 and a performing of the method 15 for a second eye of the stereoscopically captured eye region 100.

Figure 9:
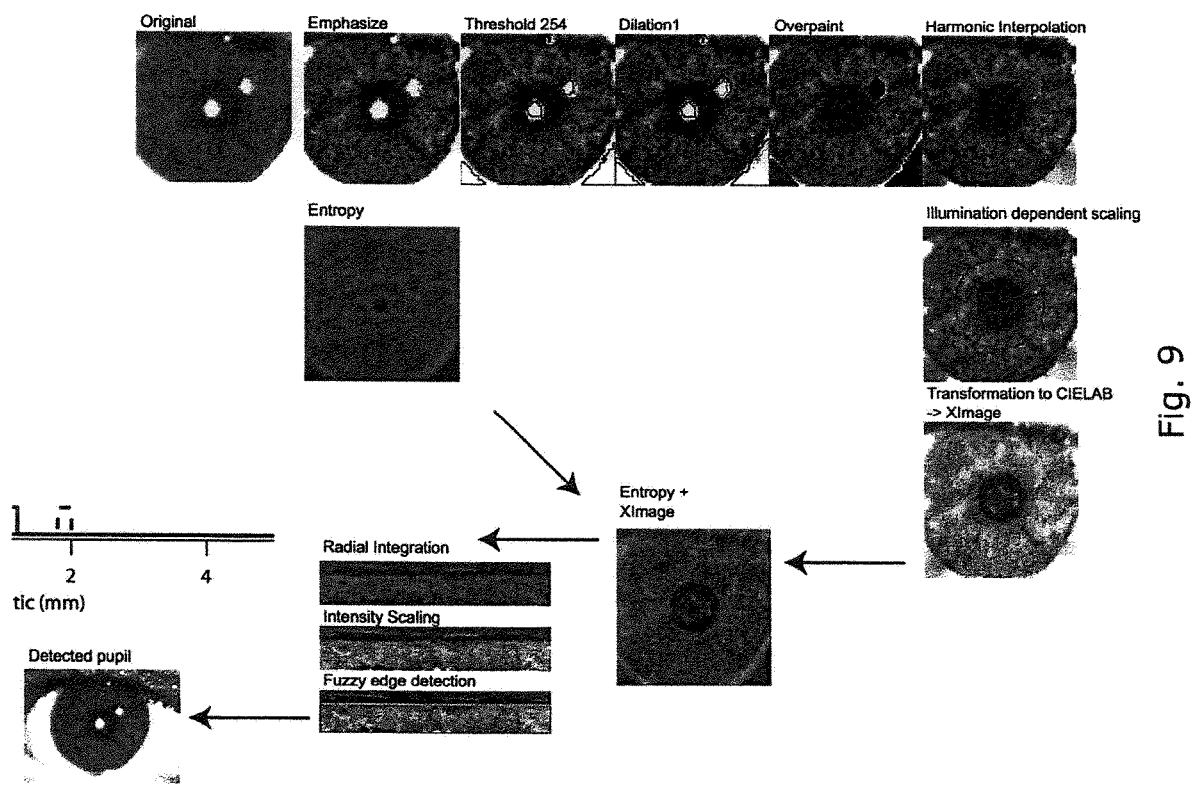
FIG. 9 shows a schematic illustration of a proposed method according to a further exemplary design of the invention.

FIG. 9 shows a schematic illustration of a proposed method according to a further exemplary design of the invention.

Here FIG. 9 shows a schematic illustration of a proposed method. Here the original image is first enhanced, for example, with respect to the contrast or the color saturation. Reflections are subsequently detected using a threshold filter. Using a vicinity method the reflection regions are filled in or painted over with the respective neighbor pixels. Furthermore, a harmonic interpolation is carried out. Furthermore, a brightness-dependent scaling is performed. The reflections are now completely removed and the pupil is reconstructed. A transformation of RGB color space into the CIELAB color space subsequently occurs. The X channel is evaluated there.

Based on an entropy method and the evaluated X channel, a radial integration method, an intensity-scaling method, and/or an edge-sensing filter, such as, for example, a fuzzy edge detection method, can be applied in order to very precisely recognize, and thus be able to measure, the pupil.

Figure 10:
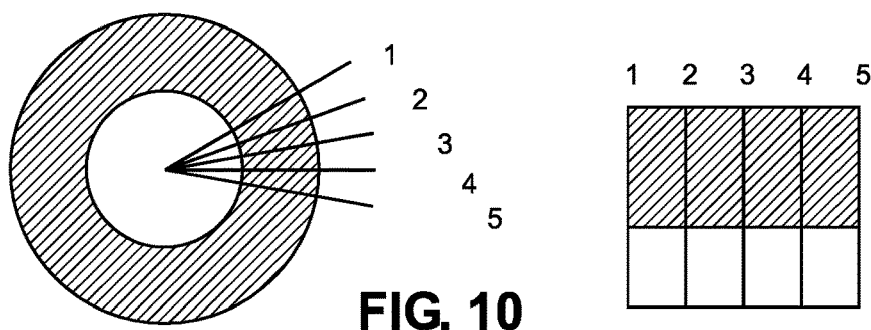
FIG. 10 shows a schematic illustration of a proposed method according to a further exemplary design of the invention.

FIG. 10 shows a schematic illustration of a proposed method according to a further exemplary design of the invention.

Here FIG. 10 shows a schematic illustration of a proposed method wherein at least the iris and the pupil are depicted in a rotationally symmetrical space (left illustration) and subsequently transferred into a Cartesian space (right illustration). For this purpose the illustration is first subdivided into segments in the rotationally symmetrical space. By way of example, in FIG. 10 five segments have been transferred into the Cartesian system. In the Cartesian space a simple diameter-determining is now possible by determining an average length of the found edges of the pupil. This now corresponds to the pupil diameter.

Figure 11:
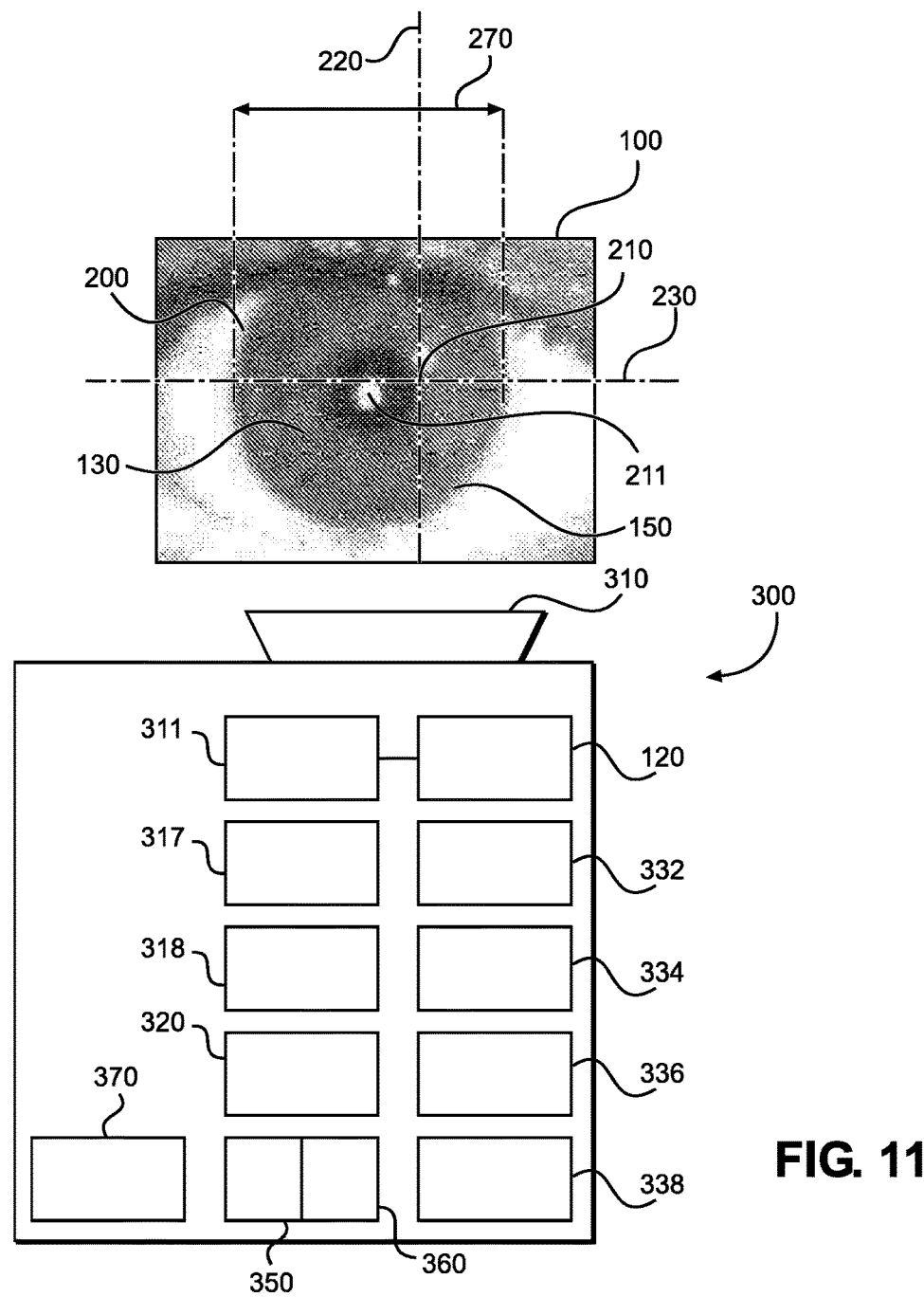
FIG. 11 shows a schematic illustration of a proposed device according to a further exemplary design of the invention.

FIG. 11 shows a schematic illustration of a proposed device according to a further exemplary design of the invention.

Here FIG. 11 shows a schematic illustration of a proposed device for highly accurate determining of a pupil diameter 270 of an eye, wherein the device includes: camera system 300 for spatial capturing of objects. Capturing means 310, for imaging stereoscopic capturing 10 of an eye region 100 of a head, using the camera system 300, for generating a first and a second stereoscopic image 110, 111 for an eye of the eye region 100. Transferring means 311, for transferring 11 of the captured eye region 100 of the head into a color space 120. First determining means 317 for determining 17 of a region 130 within the captured eye region 100 as a region 130 within a pupil 200 of the eye of the captured eye region 100. Second determining means 318, for determining 18 of a closed outer edge 140 of the region 130 within the pupil 200. Third determining means 320 for iterative determining 20 of a closed outer pupil edge 150.

In embodiments of the invention the device further includes: First determining means 332, for determining 32 a point 210 in the pupil 200. Second determining means 334, for determining 34 of a first straight line 220 through the point 210. Third determining means 336, for determining 36 of a second straight line 230, disposed orthogonal to the first straight line 220, through the point 210. Fourth determining means 338, for iterative determining 38 of a pupil center point 211.

In embodiments of the invention the device further includes: First triangulating means 350, for triangulated superposing 50 of the pupil center points 211 of the pupil 200 of the eye of the stereoscopic images 110, 111. Second triangulating means 360, for triangulated superposing 60 of the outer edges 150 of the pupil 200 of the eye of the stereoscopic images 110, 111. And a fifth determining means 370, for determining 70 of the pupil diameter 270, based on the two triangulated superpositions 50, 60. And here the device is configured to carry out an inventive method.

The inventive idea can be summarized as follows. A method and a device in this respect are provided whereby it can be possible using a stereo camera system to record the eye region of a test person, and to be able to very precisely determine the pupil diameter of each eye from these images. Due to the stereo image a plurality of two-dimensional images of the eye region arise. The images recorded are subsequently processed such that a subsequent computer-visual determining of the edge of the pupil of each eye can be performed in each image.

However, since with a stereo image it results that round regions are imaged as elliptical, the evaluated individual images are subsequently superposed and the diameter of each individual pupil is determined three-dimensionally in an extremely precise manner, taking into account the position of the stereo camera system and of the distance to the test person.

Furthermore, the resolution of the stereo camera system can also be used in order to be able to even more precisely determine the pupil diameter.

The invention further relates to a data carrier including data stored thereon or signal sequence representing data suitable for transmission via the internet, wherein the data represent a program for running on a user computer as part of a computer system for highly accurate determining of a pupil diameter 270 of an eye, using a camera system 300 for spatial capturing of objects, wherein the program is configured such that during running on the user's computer, using the camera system 300 it captures 10 an eye region 100 of a head in an imaging stereoscopic manner, wherein for an eye of the eye region 10) a first and a second stereoscopic image 110, 111 arise, and for each one of the two stereoscopic images (110, 111) the captured eye region 100 of the head is transferred 11 into a color space 120 by the user's computer, wherein it is subsequently further processed in this color space 120. The user's computer then determines 17 a region 130 within the captured eye region 100, as a region 130 within a pupil 200 of the eye of the captured eye region 100, wherein the determined region 130 within the captured eye region 100 has an image criterion 131, wherein the image criterion 131 represents a largely homogeneous image criterion. The user computer subsequently determines 18 a closed outer edge 140 of the region 130 within the pupil 200. The user's computer iteratively determines 20 a closed outer pupil edge 150, wherein the iterative determining 20 of the outer pupil edge 150 includes that the outer edge 140 is determined by circumferential determining 22 of a further region 142 outside the edge 140, along the edge 140, wherein the further region 142 is adjacent to the closed outer edge 140 of the region 130 inside the pupil 200. The user's computer iteratively examines 24 the further region 142 as to whether the further region 142 has the image criterion 131, and if at least a part of the further region 142 has the image criterion 131, the user's computer integrates 25 that part of the further region 142, which has the image criterion 131, in the region 130 within the pupil 200 of the eye, and the user's computer (26) expands the closed outer edge 140 of the region 130 within the pupil 200 to the integrated part of the further region 142. However, if the further region 132 does not completely have the image criterion 131, the user's computer establishes the closed outer edge 140 of the region 130 within the pupil 200 as the outer edge 150 of the pupil 200 of the eye, and the user's computer determines 30 a third region 160 as pupil 200 of the eye, wherein the third region 160 is that region that is completely enclosed by the outer edge 150 of the pupil 200.

The data carrier including data, or signal sequence representing data suitable for transmission via the internet, can also be adapted to the further previously specified method steps.

Furthermore, the method/the signal sequence can also be implemented as program logic.

REFERENCE NUMBER LIST

5 Calibrating of the camera system
10 Imaging stereoscopic capturing of an eye region of a head
11 Transferring of the eye region into a color space
12 Examining of the captured eye region for reflections
13 Removal of the appearing reflection
14, 15 Carrying out of the method for a first eye (14)/second eye (15) of the stereoscopically captured eye region
16 Determining of an eye in the stereoscopically captured eye region
17 Determining of a region within the captured eye region as region within a pupil of the eye of the captured eye region
18 Determining of a closed outer edge of the region within the pupil
20 Iterative determining of the closed outer pupil edge
22 Determining of a further region outside of the edge, along the edge
24 Iterative examining of the further region as to whether the further region exhibits the image criterion
25 Integrating of the part of the further region, which has the image criterion, in the region within the pupil
26 Expanding of the closed outer edge of the region within the pupil to the integrated part of the further region
28 Establishing of the closed outer edge of the region within the pupil as the outer edge of the pupil
30 Determining of a third region as the pupil
32 Determining of a point in the pupil
34 Determining of a first straight line through the point
36 Determining of a second straight line through the point
38 Iterative determining of a pupil center point
40 Determining of a first segment and of a second segment for each straight line
41 Determining of a segment corresponding to the first endpoint
42 Determining of a second endpoint of the corresponding segment
43 Determining of the corresponding segment as a line leading along the corresponding straight line starting from the corresponding first endpoint to the corresponding second endpoint
44 Iterative comparison of length of the two segments of the first straight line
45 Incrementing of a first coordinate of the point in the pupil, along the longer of the two segments of the first straight line
46 Incrementing of a second coordinate of the point in the pupil, along the longer of the two segments of the second straight line
47 Establishing the point in the pupil as the center point of the pupil
50 Triangulated superposing of the two pupil center points of the pupil of the eye of the two stereoscopic images,
60 Triangulated superposing of the two outer edges of the pupil of the eye of the two stereoscopic images
70 Determining of the pupil diameter based on the two triangulated superpositions
80 Determining of a scale
100 Eye region of a head
110 First stereoscopic image
111 Second stereoscopic image
120 Color space
130 Region within the pupil
131 Image criterion
140 Closed outer edge of the region within the pupil (abbreviated as: edge; closed outer edge)
142 Further region outside the closed outer edge of the region within the pupil (abbreviated as: further region)
150 Closed outer pupil edge
160 Third region as pupil 180 Scale
200 Pupil
210 Point in the pupil
211 Pupil center point
212 First coordinate of the point in the pupil
213 Second coordinate of the point in the pupil
220 First straight line through the point
221 First endpoint of the first segment of the first straight line
222 First segment of the first straight line
223 Second endpoint of the first segment of the first straight line
225 First endpoint of the second segment of the first straight line
226 Second segment of the first straight line
227 Second endpoint of the second segment of the first straight line
230 Second straight line through the point
231 First endpoint of the first segment of the second straight line
232 First segment of the second straight line
233 Second endpoint of the first segment of the second straight line
235 First endpoint of the second segment of the second straight line
236 Second segment of the second straight line
237 Second endpoint of the second segment of the second straight line
240 Pupil criterion
270 Pupil diameter
300 Camera system for spatial capturing of objects
310 Pixel criterion of the camera system
400 Eye model
420 Pupil model

The invention claimed is:

1. A method for determining of a pupil diameter of an eye, using a camera system for spatial capturing of objects, wherein the method includes:
Imaging stereoscopic capturing of an eye region of a head, using the camera system, wherein a first and a second stereoscopic image arise for an eye of the eye region, and
For each of the two stereoscopic images, the method further includes:
Transferring of the captured eye region of the head into a color space, and continuing the method in this color space,
Determining of a region within the captured eye region, as the entire region a pupil of the eye of the captured eye region, wherein the determined region within the captured eye region has an image criterion, wherein the image criterion represents a largely homogeneous image criterion,
Determining of a closed outer edge of the entire region of the pupil of the eye,
Iterative determining of a further region, the iterative determining of the further region including:
Circumferentially determining, with respect to the closed outer edge, the further region, with the further region being located, outside the closed outer edge, along the closed outer edge, wherein the further region is adjacent to the closed outer edge of the region within the pupil,
Iterative examining of the further region as to whether the further region has the image criterion, and
If at least a part of the further region has the image criterion:
Integrating that part of the further region, which has the image criterion, in the region within the pupil of the eye,
Expanding of the closed outer edge of the region within the pupil to the integrated part of the further region, and
If at least part of the further region does not have the image criterion:
Establishing the closed outer edge of the region within the pupil as the outer edge of the pupil of the eye,
Determining of a third region as pupil of the eye, wherein the third region is that region that is completely enclosed by the outer edge of the pupil, and
Determining a pupil diameter based on the third determined region.

2. Method according to claim 1, wherein the method further includes:
Determining of a point in the pupil,
Determining of a first straight line through the point,
Determining of a second straight line through the point, wherein the second straight line is disposed orthogonal to the the first straight line, and
Iterative determining of a pupil center point, wherein the iterative determining of the pupil center point includes:
Determining of a first segment and of a second segment for each straight line, wherein the determining of the respective segment includes:
Determining of a first endpoint of the corresponding segment, wherein the first endpoint corresponds to the point in the pupil,
Determining of a second endpoint of the corresponding segment, wherein the second endpoint corresponds to an intersection of the corresponding straight line with the edge of the pupil, and Determining of the corresponding segment as a line along corresponding straight line starting from the corresponding first endpoint leading to the corresponding second endpoint,
Iterative comparing of lengths of the two segments of the the first straight line, and
If the two segments of the first straight line are not equal in length:
Incrementing of a first coordinate of the point in the pupil along the longer of the two segments of the first straight line, and
If the two segments of the second straight line are not equal in length:
Incrementing of a second coordinate of the point in the pupil along the longer of the two segments of the second straight line, and If the two segments of the first straight line are equal in length, and the two segments of the second straight line are equal in length:
Establishing of the point in the pupil as the pupil center point of the pupil of the eye.

3. Method according to claim 2, wherein the method further includes:
Triangulated superposing of the two center points of the pupil of the eye of the two stereoscopic images,
Triangulated superposing of the two outer edges of the pupil of the eye of the two stereoscopic images, and
Determining of the pupil diameter, based on the two triangulated superpositions.

4. Method according to claim 1, wherein the method further includes:
Calibrating of the camera system for spatial capturing of objects, before the imaging stereoscopic capturing of the eye region of the head, wherein the calibrating preferably occurs based on a predefined angle and/or a predefined distance of the camera system to a reference object, and wherein during the stereoscopic capturing the head of the eye region to be captured is located at the position of the reference object.

5. Method according to claim 1, wherein the method further includes:
Determining of an eye parameter in the stereoscopically captured eye region based on a comparison of the stereoscopically captured eye region with an eye model.

6. Method according to claim 1, wherein the image criterion includes a contrast criterion.

7. Method according to claim 6, wherein the color space corresponds to a CIELAB color space.

8. Method according to claim 1, wherein the determining of the region within the captured eye region, as a region within the pupil of the eye of the captured eye region, occurs based on a pupil criterion, being a comparison with a pupil model.

9. Method according to claim 1, wherein the method further includes:
Determining of a scale, based on a distance of the camera system to the stereoscopically captured eye region of the head and of a pixel criterion of the camera system, and wherein the determining of the respective pupil diameter occurs based on the determined scale.

10. Method according to claim 9, wherein the pixel criterion of the camera system includes a pixel size or pixel width and a pixel count.

11. Method according to claim 1, wherein prior to the determining of the region within the captured eye region, as the region within the pupil of the eye of the captured eye region, the method further includes:
Examining of the captured eye region for reflections, and
Removing any appearing reflection or reflections if any, using a vicinity criterion such that image information in a region wherein the reflection appears is replaced by corresponding image information of the corresponding neighboring pixel based on the vicinity criterion.

12. Method according to claim 1, wherein the method further includes:
Carrying out of the method for a first eye of the stereoscopically captured eye region, and
Carrying out of the method for a second eye of the stereoscopically captured eye region.

13. Device for determining of a pupil diameter of an eye, wherein the device includes:
Camera system for spatial capturing of objects,
Capturing means, for imaging stereoscopic capturing of an eye region of a head, using the camera system, for generating a first and a second stereoscopic image for an eye of the eye region,
Transferring means for transferring of the captured eye region of the head into a color space,
First determining means for determining of a region within the captured eye region, as a region within a pupil of the eye of the captured eye region,
Second determining means, for determining of a closed outer edge of the region within the pupil,
Third determining means, for iterative determining of a closed outer pupil edge, and wherein
the device is configured to carry out the method according to claim 1.

14. Device according to claim 13, further including:
First determining means for determining of a point in the pupil,
Second determining means for determining of a first straight line through the point,
Third determining means for determining of a second straight line, disposed orthogonal to the first straight line, through the point,
Fourth determining means for iterative determining of a pupil center point.

15. Device according to claim 14, further including:
First triangulating means, for triangulated superposing of the pupil center points of the pupil of the eye of the stereoscopic images,
Second triangulating means, for triangulated superposing of the outer edges of the pupil of the eye of the stereoscopic images, and
Fifth determining means, for determining of the pupil diameter, based on the two triangulated superpositions.

16. Computer program product for a device according to claim 13.

17. Data carrier including a computer program product according to claim 16.

18. A computer program product, which is operable according to the method of claim 1.

* * * * *